United States Patent [19]

Chmielewski et al.

[11] Patent Number: 5,281,207
[45] Date of Patent: Jan. 25, 1994

[54] ABSORBENT PRODUCT

[75] Inventors: Harry J. Chmielewski, Auburn; John R. Cook, Tacoma; David G. Unrau, Federal Way, all of Wash.; Migaku Suzuki, Kamakura, Japan

[73] Assignee: Paragon Trade Brands, Inc., Federal Way, Wash.

[21] Appl. No.: 863,323

[22] Filed: Apr. 1, 1992

Related U.S. Application Data

[63] Continuation of Ser. No. 661,749, Feb. 26, 1991, abandoned.

[51] Int. Cl.$^5$ .................... A61F 13/15; A61F 13/20
[52] U.S. Cl. ................... 604/378; 604/368
[58] Field of Search ............ 604/368, 377, 378; 19/0.35, 0.37, 0.41, 0.43, 301, 302

[56] References Cited

U.S. PATENT DOCUMENTS

| | | | |
|---|---|---|---|
| 3,126,584 | 3/1964 | Pearson | 19/0.41 X |
| 3,781,150 | 12/1973 | Matsumura et al. | 19/302 X |
| 3,946,462 | 3/1976 | Garcia | 19/0.41 |
| 3,993,820 | 11/1976 | Repke | 428/167 |
| 4,010,752 | 3/1977 | Denny | 604/377 |
| 4,514,880 | 5/1985 | Vaughn | 19/0.35 |
| 4,540,454 | 9/1985 | Pieniak et al. | 19/302 X |
| 4,608,292 | 8/1986 | Lassen et al. | 428/131 |
| 4,673,402 | 6/1987 | Weisman et al. | 604/368 |
| 4,676,784 | 6/1987 | Erdman et al. | 604/368 |
| 4,699,823 | 10/1987 | Kellenberger et al. | 428/219 |
| 4,702,237 | 8/1987 | Lassen | 156/252 |
| 4,834,735 | 5/1989 | Alemany et al. | 604/368 |
| 4,924,556 | 5/1990 | Gilhaus | 19/0.35 |
| 4,988,345 | 1/1991 | Reising et al. | 604/368 |
| 4,994,037 | 2/1991 | Bernardin | 604/368 |

FOREIGN PATENT DOCUMENTS

| | | | |
|---|---|---|---|
| 957813 | 11/1974 | Canada | 19/302 |
| 0108637 | 5/1984 | European Pat. Off. | A61F 13/18 |
| 0212618 | 3/1987 | European Pat. Off. | A61F 13/00 |
| 0254476 | 1/1988 | European Pat. Off. | A61F 13/18 |

Primary Examiner—Randall L. Green
Assistant Examiner—Elizabeth M. Burke
Attorney, Agent, or Firm—Klarquist, Sparkman, Campbell, Leigh & Whinston

[57] ABSTRACT

An absorbent product, for use in absorbent articles, comprising an absorbent layer and a wicking layer of densified hydrophilic material. The absorbent layer comprises resilient hydrophilic fibers and superabsorbent material. The absorbent layer includes at least one area comprising a bulky fibrous structure having high void regions of low fiber density randomly distributed in the structure.

28 Claims, 1 Drawing Sheet

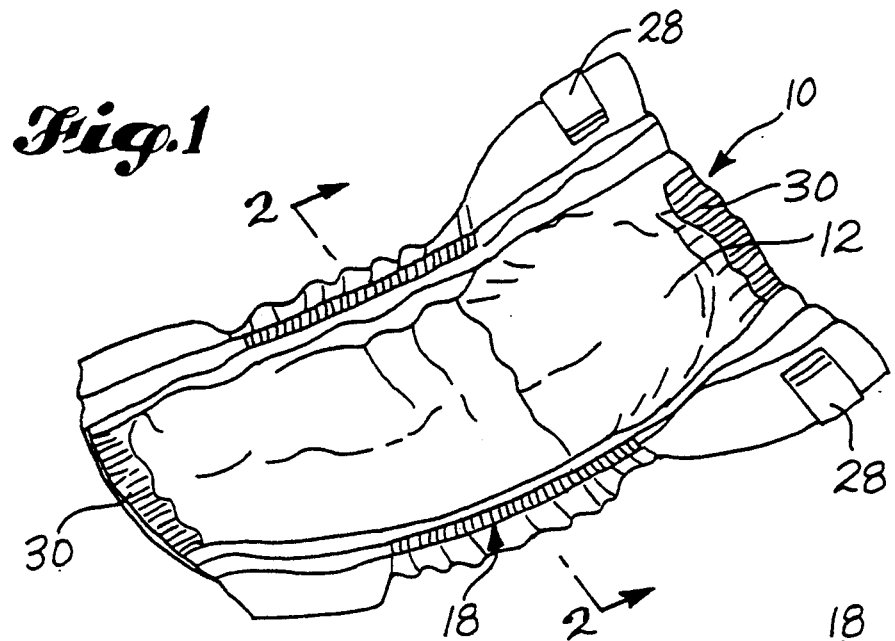
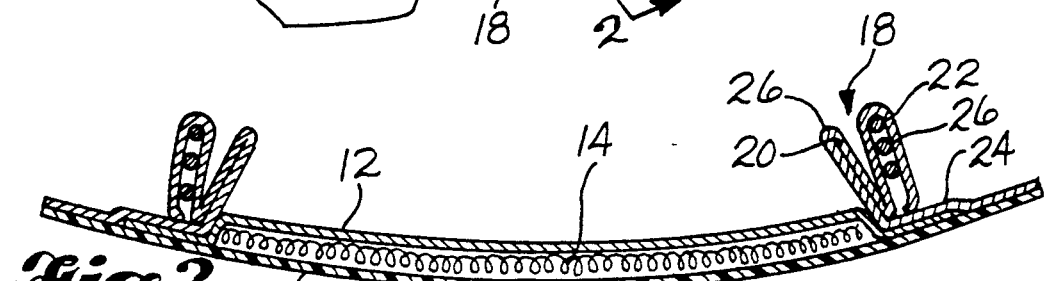
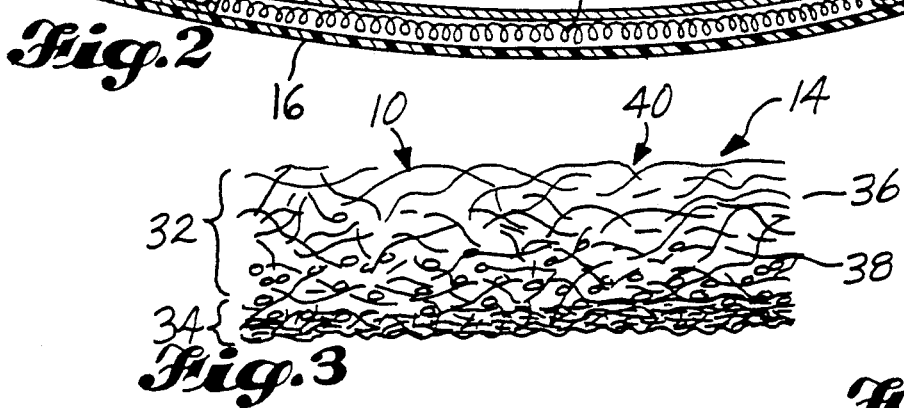
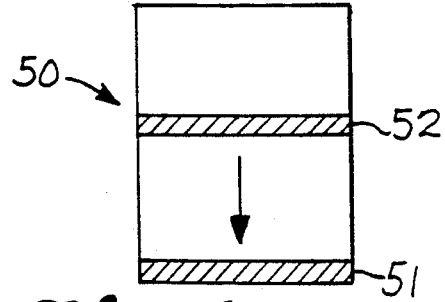 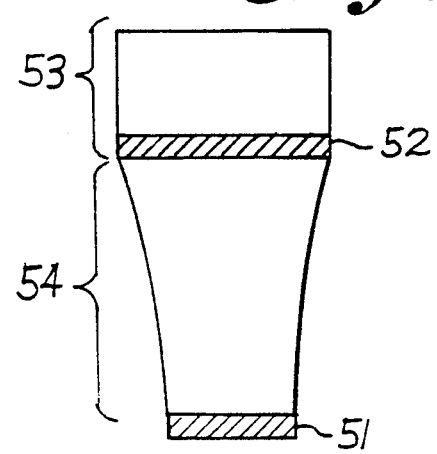

ABSORBENT PRODUCT

This application is a continuation of application Ser. No. 07/661,749, filed Feb. 26, 1991 now abandoned.

FIELD OF THE INVENTION

The present invention relates to a new and improved absorbent product containing hydrophilic fibers and superabsorbent material, and more particularly, to an absorbent product having a bulky fibrous structure wherein the fibers are loosely entangled, with high void regions of low fiber density distributed in the bulky structure.

BACKGROUND OF THE INVENTION

Disposable absorbent products have been known for some time, including such products as disposable diapers, sanitary napkins, wound dressings, bandages, incontinent pads, and the like. Such products generally incorporate absorbent structures containing superabsorbent material which absorbs and retains large quantities of liquid, even under load, large quantities of liquids. In order for superabsorbent material to function, the liquid being absorbed in the absorbent structure must be transported to the superabsorbent material. In other words, the superabsorbent material must be placed in a position to be contacted by liquid. Furthermore, as the superabsorbent material absorbs the liquid, it must be allowed to swell. If the superabsorbent material is prevented from swelling, it will cease absorbing liquids. Hence if the superabsorbent material is to function in diapers and sanitary napkins wherein the liquid to be absorbed is placed in a small void area, the structure of the absorbent layer containing superabsorbent materials, generally comprised of a mixture of hydrophilic fibers and superabsorbent materials, appears to be critical.

Over the years a number of techniques have been disclosed in an attempt to provide absorbent structures which make efficient use of the superabsorbent material. U.S. Pat. No. 4,673,402 to Weisman et al. discloses a dual-layer absorbent core wherein an absorbent acquisition layer overlays a lower fluid storage area which is preferably placed in the front two-thirds section of the absorbent core. U.S. Pat. No. 4,834,735 to Alemany et al. discloses an absorbent member wherein there is formed a liquid acquisition zone having a relatively low concentration of superabsorbent material in the front area of typical liquid deposition. U.S. Pat. No. 4,699,823 discloses an absorbent layer wherein superabsorbent particles are disposed to form a substantially continuous, non-stepwise, positive concentration gradient of superabsorbent in a thickness direction of the layer.

The aforementioned prior art has been directed toward forming a concentration gradient of superabsorbent within the absorbent structures to improve the liquid diffusion process in the absorbent structures while reducing possibilities for gel blocking to take place. Gel blocking occurs when superabsorbent particles are sufficiently close together that as they swell a layer of gel is formed and additional liquid can not penetrate that layer. These approaches are however not very effective in improving rewet properties of the absorbent structure. The term rewet describes a phenomenon that occurs when some pressure is exerted onto an absorbent layer, liquids absorbed in that layer flow or strike back to and rewet the top surface of the layer.

U.S. Pat. Nos. 4,608,292 and 4,701,237 to Lassen disclose an absorbent web wherein apertures are formed within the web to increase the available area for liquid absorption by superabsorbent. Another example of such an approach is disclosed in U.S. Pat. No. 4,676,784 to Erdman et al. Although the apertures are effective in that they provide passages for liquids to go through, they also permit liquids to strike back to a top surface of the structure, which produce a poor rewet property.

SUMMARY OF THE INVENTION

The present invention provides a new and improved absorbent product which possesses good strike-through or high liquid acquisition rate and rewet properties.

The absorbent product in accordance with the present invention comprises an absorbent layer and a densified hydrophilic material layer. The absorbent layer comprises from about 10 to about 80% by weight of hydrophilic resilient fibers and from 20 to about 90% by weight of superabsorbent material. The absorbent layer includes at least one area comprising a bulky fibrous structure having high void regions of low fiber density. The high void regions are randomly distributed in the bulky fibrous structure. The superabsorbent material is preferably disposed within a lower portion of the absorbent layer to provide the area with a bulky fibrous top layer where substantially less superabsorbent material exists. The densified hydrophilic material or wicking layer is formed of suitable hydrophilic material such as wood or synthetic pulp fibers.

The bulky fibrous structure with a plurality of high void regions of lower fiber density provides good strike-through and rewet properties. The densified hydrophilic material enhances a planar liquid transport within the absorbent product.

BRIEF DESCRIPTION OF THE DRAWINGS

FIG. 1 is a perspective view of a disposable diaper in the unfolded condition showing the top side thereof.

FIG. 2 is a cross-sectional view taken along lines 2—2 of FIG. 1.

FIG. 3 is an enlarged cross-sectional view of the absorbent product in accordance with the principles of the present invention.

FIG. 4 is a plan view of an absorbent layer formed from a resilient fibrous web containing superabsorbent material before stretching.

FIG. 5 is a plan view of the absorbent layer of FIG. 4 after stretching the resilient fibrous web containing superabsorbent material after stretching.

FIG. 6 is a cross-sectional view of another configuration of an absorbent product for use in disposable diaper in accordance with the present invention.

FIG. 7 is a photograph which shows the difference in bulk between stretched and unstretched web portions.

FIG. 8 is a schematic plan view which shows one process embodiment for manufacturing the absorbent product in accordance with the present invention.

FIG. 9 is a schematic elevated view which shows another process embodiment for manufacturing the absorbent product in accordance with the present invention.

DETAILED DESCRIPTION OF THE INVENTION

The absorbent product of the present invention will be described herein in relation to its use for disposable absorbent articles. As used in the present disclosure, the term disposable absorbent article is intended to refer to an article that is worn by an individual for absorbing and containing urine and/or fecal matter. A preferred embodiment of a disposable absorbent article, a disposable diaper, is shown in FIG. 1. It is to be understood that disposable diapers may be appropriately sized for use by infants or babies, and can further be sized for use by incontinent adults. It will be further understood that the present invention is also applicable to other disposable absorbent articles such as sanitary napkins, tampons, incontinent pads, wound dressings, absorbent wipes, and the like.

Referring to the drawings, there is illustrated in FIGS. 1-3 an exemplary disposable diaper 10 embodying an absorbent product in accordance with the principles of the present invention. Diaper 10 includes a facing or top sheet 12 formed of liquid pervious material, with the facing sheet being adapted for positioning adjacent to the wearer of the diaper. The diaper further includes an absorbent product 14, which in the illustrated embodiment, is generally rectangular, but which may be otherwise shaped, such as hourglass-shaped, T-shaped, I-shaped, or otherwise contoured.

Disposable diaper 10 further includes a backsheet 16 positioned on the side of the absorbent product 14 which is opposite the facing sheet 12. The backsheet typically comprises a liquid-impervious material, such as plastic film or sheet. Diaper 10 may be provided with a double standing gather 18 consisting of an inner gather 20 and an outer gather 22. Double standing gather 18 is preferably formed at the leg openings from a sheet of non-woven hydrophobic material 24 that is substantially impermeable to liquid while having vapor permeability characteristics, e.g. a fibrous non-woven fabric treated with silicone resin. Inner gather 20 is preferably elasticized by a monofilament rubber elements 26 extending the length thereof and outer gather 22 is preferably elasticized by a plurality of monofilament rubber elements 26 extending the length thereof. Sheet 24 is preferably glued to backsheet 16 by lines of hot melt adhesive.

As will be recognized by those familiar with the art, several different types of facing materials may be used for topsheet 12. For example, these sheets may comprise a non-woven web made of a mixture of fibers consisting predominantly of inexpensive, short, cellulosic fibers, such as wood pulp fibers or cotton linters, with the remainder of the mixture being textile length fibers. The non-woven webs may also be formed from polyester, polyethylene, polypropylene, nylon, rayon, or the like. The facing sheet may be a laminate of one or more non-woven fabrics, each having differing physical properties.

In order to secure the diaper in position, adhesive tape fasteners 28, as are well known in the art, are provided on the rearward portions of the diaper. Each of these fasteners 28 include a tab-like element having pressure-sensitive adhesive thereon which, when brought into contact with a landing area associated with the forward, outer waist portion of the diaper, secures the diaper in position. The diaper may also be provided with elasticized waistband 30, as is well known in the art.

Referring to FIG. 3, in accordance with a preferred embodiment, absorbent product 14 comprises an absorbent layer 32 and a densified hydrophilic layer of fibrous material 34. The absorbent layer 32 comprises a resilient bulky fibrous structure 36 with superabsorbent material 38 distributed within the fibrous structure. The superabsorbent material 38 is preferably in the form of a plurality of particles or globules of superabsorbent material disposed in a random and intermittent arrangement throughout the fibrous structure. The particles or globules are of a size and spacing so that they do not interfere with the absorption of liquid by adjacent particles upon expansion of the resilient fibrous structure.

The bulky fibrous structure 36 is preferably formed from resilient synthetic staple fibers, such as polyethylene, polypropylene, polyester, nylon, bicomponent fibers, and the like. Meltblown fibrous webs are also suitable. The fibrous structure includes a plurality of high void regions 40 of low fiber density randomly distributed in the structure. Notably, this structure combined with superabsorbent material has been found to provide good strike-through and rewet properties in that the bulk combined with high void regions of the fibrous structure effectively and rapidly acquires liquids and temporarily holds the liquid and effectively prevents the liquid under pressure from going back to a top surface of the fibrous structure. The fibrous web, before combination with superabsorbent material, generally has a basis weight less than about 3 oz./sq. yd. and preferably about 1.5 oz./sq. yd.

The term high void regions of low fiber density, as used herein, is intended to refer to a fibrous region with undefined boundary where substantially less resilient fibers exist as part of the bulky fibrous structure.

The provision of high void regions of low fiber density is preferably accomplished by stretching a stretchable resilient fibrous web. By stretching, fiber entanglements or fiber bondings in random locations of the web are loosened or broken to form less dense fiber areas in the web. When released from stretching forces, the web springs back to some degree due to its resilience with the result that it gains bulk and some fibers are repositioned in the less dense fiber areas to form high void regions of low fiber density in the bulky fibrous structure. The superabsorbent material 38 may be thereafter combined with the fibrous structure 36 in any number of ways. However, the most efficient way may be to provide a resilient fibrous web with superabsorbent material incorporated therein followed by stretching and releasing of the web. Generally, the resilient fibers are carded or air-laid to form a parallel, cross-parallel, or random web which, if needed, is then stabilized. Stabilization may be achieved by heat-through bonding, adhesive bonding, heat embossing, and the like. The stabilizing process is selected according to the fibers used and the process used to form the web. Other suitable procedures for forming a web include wet-laying, spun-bonding, melt-blowing, and other known techniques.

The superabsorbent material is combined with the resilient fibrous layer 32 in an amount from about 20% to about 90% by weight based on the combined weight of fibers and superabsorbent by means suitable to distribute the superabsorbent materials therein trying to minimize interference by adjacent superabsorbent materials upon swelling. If the superabsorbent material is a powder, it may be sprinkled onto the fibrous web either in dry form or the web may be moistened. If the superabsorbent material is in granular form, it may be desirable to slightly moisten the superabsorbent material before placing it in contact with the web. The superabsorbent material will contain particles which range in size from about 0.005 mm in diameter to globules that are continuous along fibers for a distance up to several inches.

Another method of placing the superabsorbent material in the web is spraying a monomer solution on the web or saturating the web with a monomer solution followed by polymerization of the monomer. One typical way to polymerize the monomer is by use of irradiation. It is desirable to place the superabsorbent material somewhat evenly throughout the fibrous web. However, even if the superabsorbent material is powder-like and in the form of a layer, it tends to function better than such a layer has in previously known products. It may be desirable to place more superabsorbent material in one area than in another and/or to place the superabsorbent material in the structure in predetermined patterns. Any superabsorbent material which absorbs large amounts of liquids is suitable for use in the absorbent layer of the present invention.

In accordance with a most preferred embodiment of the invention, droplets of the superabsorbent material are dispersed within the web by moving the web through a droplet-flicking zone and flicking droplets of the superabsorbent material, in a liquid carrier, onto one side or opposite sides of the web as the web is moved through the droplet-flicking zone. On either side of the fibrous web, a rotating brush has bristles, picking up the material, in the liquid carrier, and flicking droplets thereof as the brush rotates. The superabsorbent material is polymerized and cross-linked in situ. This method is fully disclosed in U.S. patent application Ser. No. 335,764 filed on Apr. 10, 1989, which application is assigned to the same assignee as the present invention. The disclosure in such application is incorporated herein by reference.

The superabsorbent material present in an intermittently dispersed form in the resilient fibrous web is generally a water-insoluble but water-swellable polymeric substance capable of absorbing water in an amount which is at least 10 times the weight of the substance in its dry form. The superabsorbent material is in the form of particles which may be in shape of fibers, spheres, bits of film, globules, or the like.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain. The preferred hydrophilic chains are hydrolyzed polyacrylonitrile chains and copolymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly (alkyl phosphonates), partially hydrolyzed polyacrylamides (e.g., poly (N-N-dimethyl acrylamide), sulfonated polystyrene, or a class of poly (alkylene oxide). These highly hydrophilic synthetic polymers may be modified by other chemical treatments such as cross-linking or hydrolysis. Further examples known in the art are the non-ionic hydrophilic polymers such as polyoxyethylene, poloxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combination of cations), acrylate, may be placed on the fibrous web by spraying or otherwise placing a solution thereon followed by polymerization and cross-linking, for example, by irradiation.

In addition, naturally occurring material such as gums, may be used. For instance, guar gum is suitable.

After application of the superabsorbent material, the resilient fibrous layer 32 is subjected to stretching at a preferable draw ratio of from about 50% to about 150%. For better bulk recovery after release, the web is preferably stretched in a direction that crosses fiber orientation in the web. The typical stretching direction is the CD (cross direction of other formation direction of web) for a parallel web, the MD (parallel to direction of web formation) for a cross-parallel web and the CD and/or MD for a random web. In a practical stretching operation, a resilient fibrous web containing superabsorbent material may be fed in a continuous or discrete form to a stretching station where a conventional stretcher stretches the web to a predetermined length.

Notably, this stretching has been found to increase absorbency per gram of superabsorbent material in the web in that bits of film-like particles are broken into smaller particles and more suitable spacing between adjacent particles can be obtained.

Furthermore, by stretching a selected area of the web, the final structure can be formed to comprise a relatively lower density area which corresponds to the stretched area and a relatively higher density area which corresponds to the unstretched area. This selective arrangement of density gradient within the structure is very effective in designing absorbent products for use in disposable absorbent articles.

Recovery of the web in length has been found to be dependent on the basis weights of the web and superabsorbent material, the hysteresis characteristics of the web, the draw ratio, and the like. Accordingly, it is necessary to select an appropriate combination of the material properties and process parameters to determine a target length to be desired for the final bulky fibrous structure 36.

The densified hydrophilic material or wicking layer 34 is comprised of hydrophilic fibers, such as rayon fibers, cellulosic fibers, peat moss, acrylic fibers, synthetic pulp fibers, meltblown fibers treated to be hydrophilic, or mixtures thereof. The cellulosic fibers include tissue, wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers in peat moss or mixtures thereof are placed in such a way as to form a layer in which the particles are close to one another so as to provide a higher capillary pressure to promote wicking of liquid in the plane of the layer. The wicking layer 34 can be preformed and placed next to the absorbent layer 32 or the wicking layer particles can be air-laid, mechanically entangled therewith, or wet-laid onto the absorbent layer. The wicking layer 34 may desirably be lightly-compressed against at least the stretched area of the absorbent layer 32 in order to effect stabilization thereof. In some cases, they may be lightly-compressed in the presence of moisture to form a composite so as to provide higher stabilization of the layer 34. The wicking layer 34 is preferably positioned substantially coextensive with at least the expansive surface of the stretched area of the absorbent layer 32 and has a total basis weight of from about 3 oz./sq. yd. to about 17 oz./sq. yd., more preferably from about 4 oz./sq. yd. to about 10 oz./sq. yd.

FIGS. 4 and 5 show another configuration of the absorbent layer 32 of the present invention for use in a disposable diaper. The resilient fibrous web 50 with superabsorbent material distributed in its bottom side is clamped at its one transverse end section 51 and center transverse section 52 to be stretched in an arrow direction at a draw ratio of more than 100%. After release of tension, the semi-hourglass shaped web is formed which includes about front one third section of higher density 53 and about rear two thirds section of lower density 54 which comprises a bulky fibrous structure with high void regions of low fiber density. Application of a wicking layer 34 to this absorbent layer 32 yields the absorbent product 14 suitable for use in disposable diaper, as shown in FIG. 6. The front and rear end sections of higher density have been found to function in protecting liquid leakage therethrough by gel-blocking after full absorption of liquid. FIG. 7 is a photograph which shows a bulk gain of the stretched portion of the web on its right side. The unstretched portion is shown on its left side. For this specific embodiment, the stretched portion has been observed to gain a bulk increase of 56% against 23% decrease in a basis weight over the unstretched portion. Accordingly, about 20% increase in thickness has been observed.

It has been found that at least 15% improvement in rewet values and at least 5% improvement in strikethrough values over the initial unstretched substrate can be achieved by stretching it by about 100%.

FIGS. 8 and 9 show typical schematic process flows for manufacturing the absorbent product for use in an absorbent diaper in accordance with the present invention.

In FIG. 8, a resilient fibrous parallel web 60 containing superabsorbent material on its top side is continuously fed to a stretching station 61 such as a pin tender where the fibrous web 60 is CD-stretched to a predetermined length. Here, the stretched area of the web can be selectively adjusted by changing positions of clamping or gripper means that grasp the web for stretching.

The web 60 exiting from the stretching station 61 passes a tension-release zone 62 where it gains some bulk recovery and formation of randomly-distributed high void regions of low fiber density. A pulp fiber applicator 63 casts pulp fibers onto a top surface of the fibrous web 60 so that a wicking layer may be added to the bulky fibrous structure layer. The two layers are lightly-compressed by a nip roll 64 for combination and then cut into individual absorbent product pieces 65 by a cutter roll 66. A moisturizer may be inserted between the stretching station 61 and the nip roll 64, if needed, to cause the softened surface of the superabsorbent material to provide the adhesion to the wicking layer thereby dimensionally-stabilizing the untentioned web. The individual piece 65 is next carried to a diaper assembly station where it is incorporated between a liquid-permeable topsheet and a liquid-impermeable backsheet so as for the wicking layer to face the backsheet.

In FIG. 9, the resilient fibrous parallel web 70 containing superabsorbent material on its one side is continuously fed by a driven feed roll 71 onto a vacuum roll 72 where the web 70 is transversely cut into individual pieces 73 of a predetermined width by a knife roll 74. The individual piece 73 is picked up by a pair of spaced apart transfer wheel assemblies 75, 76 from the vacuum roll 72. These wheels are placed inclined to each other so that the distance between them is greatest at the pick-up point and least at the release point. The individual piece 73 is held by each transfer wheel from the pick-up point to the release point during about 180 degrees rotation of the wheels to be CD-stretched to a predetermined length. The stretched individual piece 73 is then passed the release zone to the pulp fiber applicator as described with reference to FIG. 8. It will be readily understood that the stretch area of the fibrous web can be readily controlled by adjusting the angle of inclination of the two transfer wheels and/or the distance between the two wheels. This stretch method is fully disclosed in U.S. patent application Ser. No. 164,752 filed on Mar. 7, 1988, which application is assigned to the same assignee as the present invention. The disclosure in such application is incorporated herein by reference.

What is claimed is:

1. An absorbent product comprising
    an absorbent layer having upper and lower sides and comprising from about 10 to about 80% by weight of hydrophilic resilient fibers and from about 20 to about 90% by weight of superabsorbent material, said absorbent layer including at least one area comprising a prestretched bulky fibrous structure having high void regions of lower fiber density threw an unstretched region randomly distributed therein;
    said high void regions of lower fiber density formed from stretching of the fibrous structure which results in resilient fiber breakage and loosening, thereby forming less dense fiber areas in the absorbent layer; and
    a densified hydrophilic material placed adjacent to and at least coextensive with said at least one area of the absorbent layer to promote planar liquid transport within said absorbent layer.

2. The absorbent product as defined in claim 1 wherein
    said superabsorbent material is primarily disposed in the lower side of said absorbent layer.

3. The absorbent product as defined in claim 1 wherein
said at least one area of said absorbent layer has a concentration of superabsorbent material equal to or lower than an average superabsorbent material concentration of said absorbent layer.

4. The absorbent product of claim 3 wherein
said superabsorbent material in said at least one area has an increased absorbency per gram of superabsorbent material as compared to an average absorbency per gram elsewhere in said absorbent layer.

5. The absorbent product as defined in claim 1 wherein
said absorbent layer is a non-woven web.

6. The absorbent product as defined in claim 5 wherein
said non-woven web is a polyester web.

7. The absorbent product of claim 6 wherein
said non-woven web has an original size and,
said non-woven web is stretched 50% to 150% of its original size at said at least one area.

8. The absorbent product of claim 1 wherein
said densified hydrophilic material is underneath said absorbent layer.

9. The absorbent product of claim 1 wherein
said densified hydrophilic material is underneath said absorbent layer.

10. A disposable diaper including an absorbent product positioned between a substantially liquid impermeable backsheet and a liquid permeable topsheet, said absorbent product comprising:
an absorbent layer having upper and lower sides and comprising from about 10 to about 80% by weight of hydrophilic resilient fibers and from about 20 to about 90% by weight of superabsorbent material, said absorbent layer including at least one area comprising a prestretched bulky fibrous structure having high void regions of lower fiber density than an unstretched region randomly distributed therein;
said high void regions of lower fiber density formed from stretching of the fibrous structure which results in resilient fiber breakage and loosening, thereby forming less dense fiber areas in the absorbent layer; and
a densified hydrophilic material placed adjacent to and at least coextensive with said at least one area of the absorbent layer to promote planar liquid transport within said absorbent layer.

11. The disposable diaper as defined in claim 10 wherein
said at least one area is a central section of the absorbent product.

12. The absorbent product of claim 11 wherein
said non-woven web has an original thickness and,
said at least one area of said non-woven web has a thickness 20% greater than said original thickness after said stretching.

13. The disposable diaper as defined in claim 10 wherein
said absorbent product is divided into a front section comprising one-third of the absorbent product and a rear section comprising two-thirds of the absorbent product, and
said at least one area is primarily located in said rear section.

14. The disposable diaper as defined in claim 10 wherein
said at least one area of said absorbent layer has a concentration of superabsorbent material equal to or lower than an average superabsorbent material concentration of said absorbent layer.

15. The disposable diaper of claim 14 wherein
said superabsorbent material in said at least one area has an increased absorbency per gram of superabsorbent material as compared to an average absorbency per gram elsewhere in said absorbent layer.

16. The disposable diaper as defined in claim 10 wherein
said superabsorbent material is primarily disposed in the lower side of said absorbent layer.

17. The disposable diaper of claim 10 wherein said absorbent layer is a non-woven web.

18. The disposable diaper of claim 17 wherein said non-woven web is a polyester web.

19. The disposable diaper of claim 17 wherein
said non-woven web is stretched at a draw ratio of about 50% to 150% at said at least one area.

20. The absorbent product of claim 19 wherein
said non-woven web has an original thickness, and
said at least one area of said non-woven web has a thickness 20% greater than said original thickness after said stretching.

21. The absorbent layer of claim 19 wherein
said superabsorbent material in said at least one area has an increased absorbency per gram of superabsorbent material as compared to an average absorbency per gram elsewhere in said absorbent layer.

22. An absorbent layer comprising
an absorbent layer having upper and lower sides and comprising from about 10 to about 80% by weight of hydrophilic resilient fibers and from about 20 to about 90% by weight of superabsorbent material, said absorbent layer including at least one area comprising a prestretched bulky fibruos structure having high void regions of lower fiber density than an unstretched region randomly distributed therein;
said high void regions of lower fiber density formed from stretching of the fibrous structure which results in resilient fiber breakage and loosening, thereby forming less dense fiber area in the absorbent layer.

23. The absorbent layer of claim 22 wherein said superabsorbent material is primarily disposed on one side of said layer.

24. The absorbent layer of claim 22 wherein
said at least one area of said absorbent layer has a concentration of superabsorbent material equal to or lower than an average superabsorbent material concentration of said absorbent layer.

25. The absorbent layer of claim 22 wherein said absorbent layer is a non-woven web.

26. The absorbent layer of claim 25 wherein said non-woven web is a polyester web.

27. The absorbent layer of claim 25 wherein
said non-woven web is stretched at a draw ratio of about 50% to about 150% at said at least one area.

28. The absorbent layer as defined in claim 27 wherein
said non-woven web has an original thickness, and
said at least one area of said non-woven web has a thickness 20% greater than said original thickness after said stretching.

* * * * *

UNITED STATES PATENT AND TRADEMARK OFFICE
CERTIFICATE OF CORRECTION

PATENT NO. : 5,281,207
DATED : January 25, 1994
INVENTOR(S) : Harry J. Chmielewski et al.

It is certified that error appears in the above-indentified patent and that said Letters Patent is hereby corrected as shown below:

Column 3, line 19:  Please correct referringto" to read -- referring to--.

Signed and Sealed this

Sixth Day of December, 1994

Attest:

BRUCE LEHMAN

Attesting Officer

Commissioner of Patents and Trademarks